United States Patent [19]
Gigliello et al.

[11] 3,997,442
[45] Dec. 14, 1976

[54] METHOD OF SEPARATING AND PARTITIONING DIFFERING DENSITY PHASES OF A MULTIPHASE FLUID

[75] Inventors: Joseph F. Gigliello; Harry A. Kragle, both of Corning, N.Y.

[73] Assignee: Corning Glass Works, Corning, N.Y.

[22] Filed: Sept. 15, 1975

[21] Appl. No.: 613,076

Related U.S. Application Data

[63] Continuation-in-part of Ser. No. 452,059, March 18, 1974, Pat. No. 3,920,549.

[52] U.S. Cl. .................... 210/83; 210/DIG. 23
[51] Int. Cl.² ........................................ B01D 21/26
[58] Field of Search ............ 23/230 B, 258.5, 259, 23/292; 128/2 F, 214 R, 218 M, 272.1, DIG. 5; 210/83, 84, 514–518, DIG. 23, DIG. 24; 233/1 A, 1 R, 26

[56] References Cited
UNITED STATES PATENTS

| | | | |
|---|---|---|---|
| 2,812,231 | 11/1957 | Zar | 210/DIG. 23 |
| 3,852,194 | 12/1974 | Zine, Jr. | 210/83 |

*Primary Examiner*—John Adee
*Assistant Examiner*—Robert G. Mukai
*Attorney, Agent, or Firm*—Burton R. Turner; Clarence R. Patty, Jr.

[57] ABSTRACT

An improved method of centrifugally separating two differing density phases of a multiphase fluid and simultaneously partitioning the phases with a thixotropic material. The thixotropic material is asymmetrically positioned within a closed end of a tubular container such that the exposed or upper surface of the thixotropic material is contoured to form a space for receiving the multiphase fluid between the surface and a sidewall portion of the closed end of the tube.

1 Claim, 4 Drawing Figures

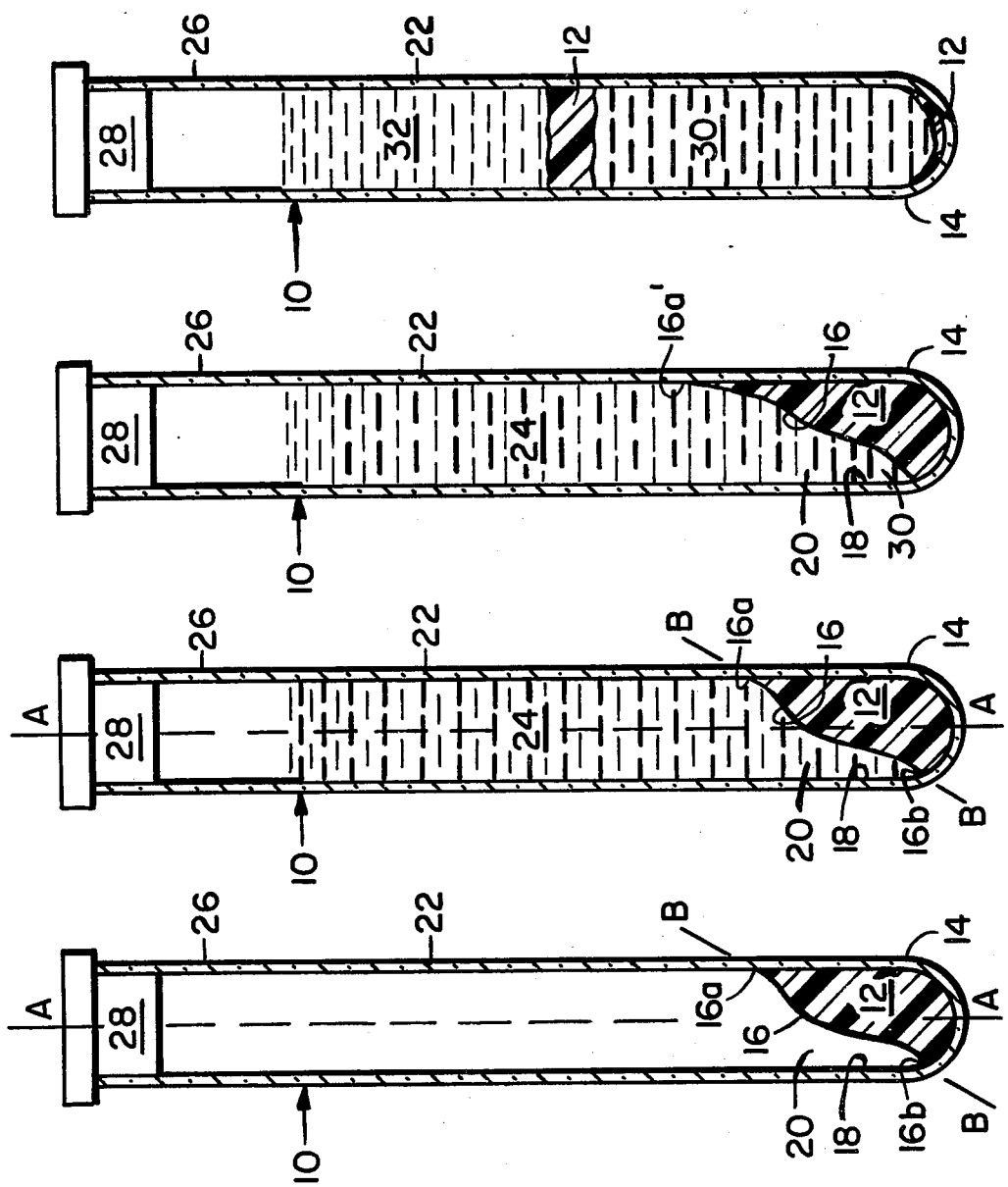

METHOD OF SEPARATING AND PARTITIONING DIFFERING DENSITY PHASES OF A MULTIPHASE FLUID

This application is a continuation-in-part of our earlier U.S. patent application, Ser. No. 452,059, filed Mar. 18, 1974, (now U.S. Pat. No. 3,920,549) and assigned to the assignee of this application.

BACKGROUND OF THE INVENTION

The present invention relates to methods of separating and partitioning differing density phases of a multiphase fluid, and more specifically, to an improved method of separating two differing density phases of a multiphase fluid and simultaneously partitioning the phases with a thixotropic material.

In U.S. Pat. No. 3,852,194 to A. R. Zine, Jr., which has been assigned to the assignee of the present application, there is described an apparatus and method for multiphase fluid collection, separation, and partitioning. The method is described in connection with collecting fresh blood and separating the blood into a serum phase and a clotted red cell phase. The method includes the steps of: providing an open-ended container with gel-like material having a specific gravity intermediate the specific gravities of two phases of a multiphase fluid to be separated; vacuum-sealing the open end of the container with a needle pierceable closure; drawing a specimen of the multiphase fluid through the closure; applying centrifugal force to the specimen and gel-like material and simultaneously forcibly moving the phases of the specimen and the gel-like material toward relative postiions within the container corresponding to their respective densities or specific gravities; terminating the application of centrifugal force after the specimen has separated into the differing density phases and a substantial portion of the gel-like material has reached a position intermediate the phases; and, at such position utilizing the gel-like material to partition the separated differing-density phases.

In one embodiment of the method of the Zine patent, the gel-like material is initially positioned adjacent the bottom end of the container such that the material is evenly distributed about the axis of the container. In particular, the gel-like material is show to be positioned adjacent a closed end of a cylindrical tubular container such that the upper surface of the gel-like material substantially lies in a plane which is normal to the axis of the tubular container. In another embodiment of the method of U.S. Pat. No. 3,852,194, the gel-like material is initially positioned on a portion of a sidewall of a tube at a distance well apart from the closed end of the tube and relatively close to the open upper end of the tube. More specifically, the material is positioned on the sidewall above the eventual interface between the separated phases.

The gel-like material utilized in the method and apparatus of the Zine patent is preferably thixotropic in its flow behavior. That is, it is substantially nonflowable at rest before centrifugation, becomes flowable during centrifugation to thereby move under the influence of centrifugation, and after centrifugation becomes substantially nonflowable again. Known types of thixotropic gel-like materials are disclosed in said Zine patent and include various mixtures of oil and finely divided siliceous dioxide. Such gels have the desirable characteristics of remaining relatively stable durig handling and storage before use and of quickly reverting to their initial nonflowable state upon termination of centrifugation.

Although the method of separating and partitioning fluid which is disclosed in the Zine patent has been satisfactory for general purposes of multiphase fluid separation, it has been found that problems may be encountered relative to the initial placement of the gel-like material specified and shown in the patent. When a thixotropic gel-like material is initially positioned at the bottom end of the tube such that the material is evenly distributed about the axis of the tube, it has been noticed that occasionally the gel-like material will remain at its initial position during normal laboratory centrifugation speeds. Even though the gel-like material has a specific gravity less than the heavier phase of the differing density fluid, nevertheless application of a normal amount of centrifugal force and even an incremental increased amount of centrifugal force sometimes did not initiate flow of the gel-like material from its initial bottom-center position.

Also, in connection with the separation of blood into a heavy phase including clotted red cells and a light phase consisting of serum, it has been found that flow of the gel-like material through central portions of the blood results occasionally in excessively high lactic dehydrogenase (LDH) content of the separated serum. As is clearly shown in the drawings of the Zine patent, initial positioning of the gel-like material at the bottom of the tube symmetrically about the axis of the tube results in flow of the gel-like material through central portions of the multiphase fluid. Although the hydrodynamics of the flow of multiphase fluids and gel-like material during centrifugation are not fully understood by the applicants, hereof, it has been determined that the flow of gel-like material from a position below a body of red cells within the tube through central portions of such body of red cells results in excessive rupturing of the red cells and the consequent release of LDH from the red cells.

Another problem associated with the positioning of the thixotropic partitioning material symmetrically at the bottom of the container relates to the quality of the seal produced by the thixotropic material between the separated phases. The movement of some thixotropic materials from such a position has been found to be sometimes so sluggish that, unless the duration or speed of centrifugation is increased, the thixotropic material may not form an adequate seal between the separated phases. By an adequate seal, it is meant that the seal must be able to remain intact while the lighter, uppermost phase is being poured or decanted from the container. It will be appreciated that an increase in the speed of centrifugation or the duration of centrifugation over that customarily used in the separation of blood is not desirable because such increases are likely to cause excessive hemolysis or rupturing of the cellular constituents of blood.

Regarding the positioning of thixotropic fluid at the sidewall of the container above the eventual interface between the separated light and heavy phases, we have found that such positioning is difficult to maintain, because thixotropic partitioning material positioned on the sidewall tends to slump and spread out over the sidewalls during handling and shipping prior to centrifugation. Thus, such elevated positioning on the sidewall produces an unprofessional appearance.

The method of the present invention responds to each of the previously described problems in a manner so as to completely eliminate any further concern regarding such problems.

SUMMARY OF THE INVENTION

The present invention provides an improved method of separating and partitioning heavy and light phases of a multiphase fluid. The method includes an initial step of positioning a quantity of thixotropic material asymmetrically within the closed end of a tubular container, such that the thixotropic material has an upper surface which is inclined relative to the sidewall of the container, thereby forming a downwardly extending fluid-receiving space between the upper surface of the thixotropic material and an opposing sidewall portion of the closed end of the container. A quantity of multiphase fluid, such as blood, having a light phase and a heavy phase, is introduced into said container through an open end thereof. The container is then inserted into the centrifugation apparatus; and the multiphase fluid and thixotropic material are subjected to a centrifugal force to urge the multiphase fluid toward the closed end of the container into the fluid-receiving space formed by the upper surface of the thixotropic material and the opposing portion of the container sidewall, and to thereby simultaneously force the thixotropic material to flow from an upper extent of the upper surface thereof toward the open end of the container through peripheral portions of the multiphase fluid. By continuing to subject the multiphase fluid and thixotropic material to the centrifugal force, the heavy and light phases of the fluid are separated and simultaneously the thixotropic material is moved to a position interposed between the phases. Finally, upon termination of the centrifugal force, a partition is established between the separated phases by the thixotropic material. In a preferred embodiment, the method of the present invention further includes the steps of evacuating the container, and sealing the open end of the container with a removable needle-pierceable stopper to provide a closed fluid collection chamber therewithin. By using a double ended needle, the evacuated, closed container may be used to siphon blood through the stopper.

Other advantages and features of the instant invention will be understood from the following description in conjunction with the attached drawings.

BRIEF DESCRIPTION OF THE DRAWINGS

FIG. 1 illustrates a fluid collection and partitioning assembly, ready for use, having a quantity of thixotropic material positioned asymmetrically at a closed end of the container.

FIG. 2 is the assembly of FIG. 1 after the introduction of a multiphase fluid thereinto.

FIG. 3 depicts the step of applying centrifugal force to initiate the separation of two phases of the multiple phase fluid and the movement of the thixotropic material toward the eventual interface between the phases.

FIG. 4 illustrates the positions of the separated phases and the thixotropic material upon termination of the centrifugation.

DESCRIPTION OF A PREFERRED EMBODIMENT

A preferred embodiment of the improved method of separating and partitioning differing density phases of a multiphase fluid is illustrated in FIGS. 1 through 4. As shown in FIG. 1, a tubular container 10, having a sidewall 22 preferably of cylindrical tubular form, is provided with a body of thixotropic gel-like material 12. The thixotropic material is positioned asymmetrically adjacent a closed end 14 of the container 10 such that the upper surface 16 of the thixotropic material together with contiguous and opposing inner surface portion 18 of the closed end 14 forms a downwardly extending fluid-receiving space or recess 20. The upper surface 16 of the thixotropic material 12 is inclined relative to the cylindrical sidewall 22. As shown in axial cross-section in FIG. 1, a straight line B—B drawn from an upper extent or extremity 16a of the surface 16 to a lower extremity 16b of the surface 16 will intersect a plane contiguous with the axis A—A of the sidewall 22 to form oblique lesser included angles with such plane. That is to say, the upper surface 16 may be a planar or curvilinear surface which is generally downwardly inclined relative to the sidewall 22 of the container 10.

Next, as depicted in FIG. 2 a preselected quantity or body of a multiphase fluid 24 is supplied to the container 10. When the multiphase fluid is blood, it is a customary practice in the blood collection art to use an evacuated container having needle-pierceable closure means for forming a vacuum-tight seal within an opening in the container, and to aspirate or siphon blood into the container by means of a double-ended needle. The present embodiment is described in connection with blood collection, separation and partitioning. Thus, the container 10 shown in FIG. 1 is evacuated to a low partial pressure, and a needle-pierceable or puncturable stopper or closure 28 is inserted into an open end 26 of the container 10 to form a vacuum-tight seal therewith. Blood is siphoned into the evacuated container through the open end 26 by using a double-ended needle or cannula, with one end of the needle being inserted into a blood vessel of a patient and the other end thereafter being pushed through the stopper 28.

If it is desired to separate the blood into serum and clotted red cell phases, the blood is allowed to coagulate within the container, with the blood thus forming a light serum phase intermixed with a heavy clotted red cell phase. The light serum phase is shown in FIGS. 2–4 as light dashed lines. The heavy clotted red cell phase is depicted by heavy dashed lines and includes fibullar and cellular matter (e.g., fibrin, red cells, etc). The heavy red cell phase has a specific gravity of approximately 1.08–1.09 and the light serum phase has a specific gravity of approximately 1.02–1.03. It will be appreciated to those skilled in the art of blood separation that an anticoagulant may be used when it is desired to separate plasma, rather than serum, from blood. The specific gravity of whole blood is approximately 1.05–1.06.

The thixotropic material 12 may be a mixture of a liquid, such as silicone oil, and a filler, such as a silicaeous dioxide. It is chemically inert or noninteractive with the multiphase fluid 24 and has a density which is intermediate the phases to be separated. A thixotropic material suitable for separating serum from blood has a specific gravity ranging from 1.035–1.06, with the preferred range of 1.04–1.055. Various thixotropic materials suitable for blood separation and partitioning are now well known to those skilled in the art; and various specific compositions are given, for example, in U.S. Pat. Nos. 3,852,194 and 3,780,935.

The term, thixotropic, as used herein, signifies a flow behavior which is non-Newtonian and which is substantially non-flowable or semi-rigid at rest. A thixotropic fluid or material will remain at the closed end 14 of the tube during handling before centrifugation, will become flowable and flow during centrifugation, and will revert to a substantially non-flowable state after termination of centrifugation.

After coagulation, the container 10 is inserted, closed end 14 first, into a receptacle or basket of a centrifugation apparatus or centrifuge. As shown in FIG. 3, the multiphase fluid 24 will be received within the space or recess 20 formed by the inclined upper surface 16 of the thixotropic material and the proximal and opposing inner surface portion 18 of the container closed end 14. Next, centrifugal force is applied to the contents of the container by swinging the receptacle holding the container around an axis of rotation of the centrifuge; the closed end 14 of the container 10 is held or assumes a position which lies radially outwardly from the axis of rotation relative to the stopper open end 26 of the container. Accordingly, the multiphase fluid or blood 24 is centrifugally forced into the fluid-receiving space 20 defined at one side by the upper surface 16 of the thixotropic material, and the material 12 itself is centrifugally forced against the closed end 14 of the container. Quickly, after the start of the centrifugation, a portion of the heavy red cell phase, indicated by numeral 30 in FIG. 3, separates from the blood and is received within the fluid-receiving space 20.

The heavy red cell phase 30, being substantially heavier than the thixotropic material 12, imparts energy to the thixotropic material at the surface 16 thereof and displaces some of the material 12 toward the stoppered end 26. Due to the initial upwardly and sideways inclined surface 16 of the material 12, and also the forces exerted by the blood 24 on the surface 16, the material 12 initially flows from the vicinity of the upper extremity or extent 16a of the upper surface 16. Thereafter, heavy phase 30 continues to accumulate within the space 20, while the material 12 more or less steadily flows along portions of the sidewall 22 from an elevated upper extent 16a' of the material 12.

The initial positioning of the thixotropic material assymetrically at the bottom of the container in the manner thus described has been found to, first, assure the rapid initiation of flow of the thixotropic material at normal or customary centrifugation speeds used for many years in blood separation practices, and, second, to cause the thixotropic material to flow through peripheral portions of the container, that is, along portions of the sidewall 22 of the container 10. Such rapid initiation and peripheral flow results in less hemolysis or rupturing of red cells than was associated with the previous method wherein the material was initially positioned symmetrically at the bottom end of the container and flow through central portions of the blood.

As shown in FIG. 4, centrifugation is continued until a substantial portion of the material 12 has risen to a position located above the heavy clotted red cell phase 30 and below a light serum phase 32, and until the multiphase fluid or blood 24 has completely separated into the two phases 30 and 32. Due to the rapid initiation of flow, the ease of flow along the sidewall of the container, and the displacement effect on the thixotropic material 12 by the heavier phase 30 achieved by the initial asymmetric positioning of the material 12 below the eventual interface between the phases to be separated, substantially all of the thixotropic material 12 will flow to the interface position between the phases. Should centrifugation be terminated before all of the material 12 has been displaced, the remainder of the material 12 will be located below the partition formed by the material 12, thus minimizing concern about contamination of the light serum phase 32 with the thixotropic material 12.

Upon termination of centrifugation, the thixotropic material 12 forms a semi-rigid seal with adjacent portions of the inner surface of container sidewall 22, which seal is sufficient to withstand the pressures exterted by heavy phase 30 when the container is inverted. Thus, when it is desired to remove the light phase 32, such phase may be simply decanted from the container.

It will be appreciated that it is not necessary that the container 10 have a cylindrical sidewall 22 or a closed end 14 formed by an integral bottom wall, which features are shown in the drawings. Sidewall 22 may, for example, have a conical contour. Also, the closed end 14 may be formed by a removable stopper or closure inserted into an open end of a cylindrical tube. Furthermore, it is not essential that the open end 26 be vacuum-sealed with a stopper; although it is customary or typical to do so in blood separation practice, any method may be used to supply multiphase fluid to the container.

Although the present invention has been described in connection with separating a light serum phase from blood, it will be appreciated that any differing density blood phases, including, for example, plasma or cellular material, such as platelets or white cells, may be separated and partitioned by the present new and improved method. Moreover, the advantages of the present method, especially that of the rapid initiation of flow of the thixotropic material, may be achieved in the separation of multiphase fluids other than blood.

While the invention has been described in connection with a preferred embodiment thereof, it is to be understood that the present disclosure is illustrative rather than restrictive and that further modifications may be resorted to without departing from the spirit of the invention or the scope of the claims which follow.

We claim:

1. An improved method of separating blood into a light phase and a heavy red cell phase including the steps of, positioning a quantity of thixotropic material at a closed bottom end of a tubular container, said material being chemically inert with respect to blood and having a specific gravity intermediate the specific gravities of the phases of blood to be separated; introducing into said container a quantity of blood to be separated; subjecting said blood and said thixotropic material to a centrifugal force to urge said blood to separate into a light phase and a heavy red cell phase and to simultaneously move said material to a position between said phases; and after said phases are separated and a substantial amount of said material has formed a partition between said separated phases, terminating the centrifugal force, wherein the improvement comprises the steps of, initially positioning said thixotropic material asymmetrically across said closed bottom end and upwardly along a sidewall adjacent said bottom end such that said thixotropic material has an upper surface which is upwardly and sideways inclined relative to the sidewall of the container to form a blood-receiving space between upper and lower extremities of said upper surface and an opposing sidewall portion adjacent said upper surface; and during the step of applying centrifugal force, urging the heavy red cell phase downwardly toward said closed end and into said blood-receiving space, and simultaneously moving said thixotropic material from the upper extremity of said material upwardly through peripheral portions of the blood along a portion of said container sidewall, whereby the thixotropic material will move rapidly from its initial position and flow through the periphery of the blood with minimal hemolysis of red cells due to collision of the downwardly moving heavy red cell phase and the upwardly moving thixotropic material.

* * * * *